US00RE39079E

(19) United States
(12) Reissued Patent
Tanner et al.

(10) Patent Number: US RE39,079 E
(45) Date of Reissued Patent: Apr. 25, 2006

(54) FILM FORMING COMPOSITIONS COMPRISING MODIFIED STARCHES AND IOTA-CARRAGEENAN AND METHODS FOR MANUFACTURING SOFT CAPSULES USING SAME

(75) Inventors: Keith Edward Tanner, Safety Harbor, FL (US); Peter Robert Draper, LaSalle (CA); John J. Getz, Delray Beach, FL (US); Stephen W. Burnett, Clearwater, FL (US); Elizabeth Youngblood, Valrico, FL (US)

(73) Assignee: R.P. Scherer Technologies, Inc., Las Vegas, NV (US)

(21) Appl. No.: 10/764,382

(22) Filed: Jan. 22, 2004

Related U.S. Patent Documents

Reissue of:
(64) Patent No.: 6,340,473
Issued: Jan. 22, 2002
Appl. No.: 09/608,853
Filed: Jun. 30, 2000

U.S. Applications:
(60) Provisional application No. 60/142,704, filed on Jul. 7, 1999.

(51) Int. Cl.
*A61K 9/48* (2006.01)

(52) U.S. Cl. ..... 424/451; 424/452; 514/777; 514/778; 514/782

(58) Field of Classification Search ..... 424/451, 424/452, 453, 454, 455, 489, 490; 514/777, 514/778, 482
See application file for complete search history.

(56) References Cited

U.S. PATENT DOCUMENTS

| | | | | | |
|---|---|---|---|---|---|
| 3,865,603 | A | * | 2/1975 | Szymanski et al. | 108/145.1 |
| 4,026,986 | A | * | 5/1977 | Christen et al. | 264/301 |
| 4,479,973 | A | * | 10/1984 | Holley | 426/573 |
| 5,051,304 | A | * | 9/1991 | David et al. | 428/402.2 |
| 5,264,223 | A | * | 11/1993 | Yamamoto et al. | 424/451 |
| 5,342,626 | A | * | 8/1994 | Winston et al. | 424/461 |
| 5,431,917 | A | * | 7/1995 | Yamamoto et al. | 424/451 |
| 5,614,217 | A | * | 3/1997 | Chiprich et al. | 424/451 |
| 5,756,123 | A | * | 5/1998 | Yamamoto et al. | 424/451 |
| 6,582,727 | B1 | * | 6/2003 | Tanner et al. | 424/451 |

FOREIGN PATENT DOCUMENTS

| | | | |
|---|---|---|---|
| EP | 0 141 374 | * | 5/1985 |
| EP | 0 547 551 A1 | * | 12/1992 |
| EP | 0 592 130 A2 | * | 4/1994 |
| EP | 0 714 656 A1 | * | 6/1996 |
| EP | 0 882 449 A1 | * | 12/1998 |
| EP | 0 592 130 B1 | * | 4/1999 |
| GB | 2 214 920 A | * | 9/1989 |
| JP | SH060-12943 | * | 1/1985 |
| JP | 61-10508 | * | 1/1986 |
| JP | 61010508 A | * | 1/1986 |
| JP | 63-164858 | * | 7/1988 |
| JP | 1-143827 | * | 9/1989 |
| JP | 4-243818 | * | 8/1992 |
| JP | 05065222 A | * | 3/1993 |
| JP | HE15-310529 | * | 11/1993 |
| JP | HE19-25228 | * | 1/1997 |
| WO | 95/35100 | * | 12/1995 |
| WO | 00/10538 | * | 3/2000 |
| WO | 00/18835 | * | 4/2000 |

OTHER PUBLICATIONS

"Diffusion Characteristics and Properties of Chitosan Coacervate Capsules", Process Biochemistry, 26 (1991) pp. 75–81.*

Chemical Abstracts 63—Pharmaceuticals, vol. 126, No. 15, 1997.*

* cited by examiner

*Primary Examiner*—Michael G. Hartley
(74) *Attorney, Agent, or Firm*—William H. Dippert; Andrew G. Rozycki; Donald O. Nickey

(57) ABSTRACT

Disclosed herein are compositions comprising a modified starch and a carrageenan, especially iota-carrageenan, where the compositions are suitable for use in manufacturing soft capsules.

6 Claims, No Drawings

FILM FORMING COMPOSITIONS COMPRISING MODIFIED STARCHES AND IOTA-CARRAGEENAN AND METHODS FOR MANUFACTURING SOFT CAPSULES USING SAME

Matter enclosed in heavy brackets [ ] appears in the original patent but forms no part of this reissue specification; matter printed in italics indicates the additions made by reissue.

RELATED APPLICATIONS

This application is a continuation-in-part application and is based on U.S. Provisional Application Ser. No. 60/142,704; filed Jul. 7, 1999.

FIELD OF THE INVENTION

This invention relates to capsules and, more specifically, to soft capsules typically made using a rotary die apparatus. More specifically, it relates to novel compositions that are capable of forming films from which soft capsule shells can be made.

BACKGROUND OF THE INVENTION

Encapsulation within a soft capsule of a solution or dispersion of a nutritional or pharmaceutical agent in a liquid carrier offers many advantages over other dosage forms such as compressed, coated or uncoated solid tablets or bulk liquid preparations. Encapsulation of a solution or dispersion permits accurate delivery of a unit dose, an advantage which becomes especially important when relatively small amounts of the active ingredient must be delivered, as in the case of certain hormones. Such uniformity is more difficult to achieve via a tableting process wherein solids must be uniformly mixed and compressed, or via incorporation of the total dose of active ingredient into a bulk liquid carrier which must be measured out prior to each oral administration.

Soft capsules, most commonly, soft gelatin capsules, provide a dosage form which is more readily accepted by patients, since the capsules are easy to swallow and need not be flavored in order to mask the unpleasant taste of the active agent. Soft capsules are also more easily transported by patients than bulk liquids, since only the required number of doses need be removed from the package.

Soft encapsulation of drugs further provides the potential to improve the bioavailability of pharmaceutical agents. Active ingredients are rapidly released in liquid form as soon as the gelatin shell ruptures. Complete disintegration of the capsule is not necessary for the active ingredients to become available for absorption, unlike the case of tableted compositions. Also, relatively insoluble active ingredients can be dispersed in a liquid carrier to provide faster absorption.

Traditionally, both soft and hard-shell capsules have been manufactured using mammalian gelatin as the material of choice for producing the capsule envelope. The rotary die process developed by Robert Scherer in 1933 for producing one piece soft capsules utilized the unique properties of gelatin to enable a continuous soft capsule manufacturing process. The inventive, gelatin-free composition disclosed in this patent application is especially useful in the rotary die method of soft capsule manufacture.

Conventional manufacturing of soft capsules using the rotary die process utilizes mammalian gelatin in a process essentially as follows. Dry gelatin granules are combined with water and suitable plasticizers and the combination is then heated under vacuum to form a molten gelatin mass. The gelatin mass is held in its molten state while being formed or cast as films or ribbons or casting wheels or drums. The films or ribbons are fed under a wedge and between rotary encapsulation dies. Within the encapsulation dies, capsules are simultaneously formed from the films or ribbons, filled, cut and sealed. The seals are formed via a combination of pressure and heat as the capsule is filled and cut. Rotary die manufacture of soft gelatin capsules is disclosed in detail in The Theory and Practice of Industrial Pharmacy (Lachman, Lieberman and Kanig, Editors), 3$^{rd}$ Edition, published by Lea & Febiger. A good description of gelatin encapsulation techniques can also be found in WO 98/42294 (PCT/GB98/00830).

Gelatin formulations used to produce films suitable for making capsules within the rotary die process typically contain between 25% to 45% by weight mammalian gelatin. Levels below 25% by weight tend to lead to poor sealing of the capsule. The physical properties of the gelatin film are critical to the economic production of soft capsules. For example, the film must be strong enough to survive manipulation in the encapsulation machine, provide good sealing properties at temperatures below the melting point of the film, evidence rapid dissolution in gastric juices, and have sufficient elasticity to allow for the formation of the capsule. The wholly non-animal composition of the present invention meets all of these requirements without the use of mammalian gelatin, and surprisingly evidences several improved properties.

The composition according to the present invention, like mammalian gelatin, has many properties that favor its use in soft capsule manufacture. One important property of the inventive compositions with respect to the rotary die process is the ability of the compositions to be cast to form films that are mechanically strong and exhibit elasticity sufficient to allow the film to stretch during filling. In other words, the inventive films have dimensional stability, elasticity and strength adequate for use in a continuous commercial process.

Another important and unique property of the inventive compositions is that the films forming the two halves of the capsule will fuse together during the filling and cutting process when subjected to sufficient pressure and elevated temperature. This fusing together relies on a particular property of the films that allows fusion under conditions of elevated temperature, supplied by the injection wedge, and pressure, supplied by the rotary cutting dies. The temperature at which fusion of two opposing films occurs should be below the melting point of the film, i.e., the fusion or sealing temperature is less than the melting point of the film composition. It has proven difficult to find this combination of properties in other polymer systems. Thus, most proposed substitutes for mammalian gelatin have failed due to a lack of one or more of these properties. This is the main reason why mammalian gelatin has been used almost exclusively as the shell forming material in soft capsule manufacture.

The property of fusion temperature being lower than melting temperature is crucial to the sealing of capsules using the continuous rotary die process. If the fusion and melting temperatures are about the same, the film will nearly completely melt as it passes through the wedge and the rotary die. At this temperature, the film loses its structure. As a result, capsules cannot be produced.

Disadvantages of mammalian gelatin includes the cost and continuity of supply. Gelatin has a variety of other drawbacks. For example, bovine sources are somewhat unattractive to individuals that prefer vegetarian food sources. Also, gelatin is prone to cross-linking, either caused by aging or due to reaction with compounds such as aldehydes. Cross-linking reduces the gelatin insoluble in gastric fluids, a generally undesirable quality for soft capsules. Thus, there is a need in the soft capsule industry for a replacement for the gelatin based compositions.

Other hydrocolloids form films but they lack the attributes of mammalian gelatin required to allow their use in the rotary die process. For example, a variety of modified food starches such as those available from Grain Processing Corporation as Pure-Cote®, are low viscosity starches that provide film-forming and adhesive properties. Such starches form clear, flexible films that are fast drying and flavor free. These materials are suitable as binders for seasonings on snacks and cereals and as smooth, glassy coating agents for confections and baked goods. However, these materials are unable to form hydrated films with the requisite strength and elasticity required for use in the rotary die process. Further, films made entirely from starch have insufficient elasticity and strength to be transferred from the casting drum to the rotary dies. Also, the films adhere too tightly to the casting drum, further diminishing transferability. Thus, compositions are needed that mimic the behavior and characteristics of mammalian gelatin while overcoming its shortcomings.

BACKGROUND ART

Japanese Patent Application Kokai Publication No. 63-164858 discloses a composition for the outer skin of soft capsules that allows the filling of hydrophilic materials into the capsule. The composition is a mixture of at least one natural polysaccharide selected from alginic acid, alginic acid derivatives, agar, locust bean gum, carrageenan, guaic gum, tamarind seed polysaccharide, pectin, xanthan gum, glucomannan, chitin, pluran, and cyclodextrin; and at least one substance selected from polyvalent alcohols, sugar alcohols, monosaccharides, disaccharides, and oligosaccharides. The oligosaccharides are described as enzyme and acid decomposition products of sweet potato, potato, corn and the like. While carrageenan is disclosed, there is no distinction made between the various forms of carrageenan (i.e., iota versus kappa). Further, there is no suggestion that the combination of two gelling agents, iota-carrageenan and a modified starch having a hydration temperature below about 90° C. would advantageously produce a soft capsule having outstanding physical properties. Further, there is no disclosure or suggestion that a weight ratio of modified starch to iota-carrageenan of at least 1.5:1 is required to produce a film that can be used in a rotary die encapsulation machine to make soft capsules.

International Patent Application No. PCT/FR98/01744 (WO 97/07347) discloses a composition for the manufacture of soft and hard capsules that uses iota-carrageenan as the only gelling agent at concentrations of greater than 5% by weight. This reference does disclose the use of starches and surfactants in the composition at levels of up to 20% by weight for the purpose of accelerating the disintegration of the capsule after contacting gastric juices. No specific teaching on the type of starch is given, other than substances such as wheat, rice, maize or manioc starch which may or many not have been modified, may be used. This reference fails to suggest or disclose the use of gelling starches and iota-carrageenan at weight ratios of at least 1.5:1 to form films useful in making soft capsules, wherein the starch is a modified starch with a hydration temperature of less than 90° C.

U.S. Pat. No. 5,342,626 to Winston et al. discloses a composition comprising gellan, carrageenan and mannan gums for producing soft capsules. This patent further discloses that the tri blend of gums can be combined with additional ingredients to form a film-forming polymer composition. This reference, however, fails to disclose the benefits that can be arrived at through the use of iota-carrageenan with certain modified starches.

Japanese Patent Application No. HE19-25228 discloses a soft capsule film having an essential components agar and water-soluble high polymers, such as the carrageenans. This reference fails to suggest or disclose the combination of iota-carrageenan with a modified starch having a hydration temperature below about 90° C. to form films that have outstanding properties in the preparation of soft capsules.

In similar fashion, Japanese Patent Application Disclosure No. HE15-310529 discloses a capsule forming film comprising agar and carrageenan. The reference points out that kappa carrageenan was found to be preferable. This reference does not make any mention of modified starches being incorporated into the film forming composition.

Japanese Public Patent Disclosure Bulletin No. 61-10508 disclose capsules made from polysaccharides which contain carrageenan and a base which contains multivalent alcohols. The multivalent alcohols include sorbitol, ethylene glycol, glycol, glycerin and the like. No mention is made of iota-carrageenan nor of modified starches.

Another reference suggesting the use of kappa-carrageenan to form capsules is seen in Japanese Patent Application Disclosure No. SHO60-12943. This reference teaches the exclusive use of kappa carrageenan in concentrations of about 1 to about 12% by weight. This reference also suggest that suitable plasticizers or gelatins can be included for increasing film strength.

PCT Application WO 00/10538 to Banner Pharmacaps discloses a gelatin free capsule comprising:

a) 8–50% by weight of a water dispersible or water-soluble plasticizer;

b) 0.5–12% by weight kappa carrageenan;

c) 0–60% by weight dextrins; and d) 1–95% by weight water wherein the kappa carrageenan comprises at least 50% by weight of all gums forming or contributing to formation of thermo-reversible gels in the composition. This application does not suggest the combination of a film-forming starch and iota-carrageenan to produce a film of exceptional properties for the formation of soft capsules.

U.S. Pat. No. 5,089,307 to Ninomiya et al. discloses a heat sealable, edible film comprising a film layer consisting essentially of: 1) a water soluble polysaccharide composed chiefly of carrageenan; 2) a polyhydric alcohol; and 3) water. The film of this patent has a water content of not greater than 25% by weight and a weight ratio of the polyhydric alcohol to the water soluble polysaccharide being in the range from 1:5 to 1:1. While this reference does mention all three (3) forms of carrageenan, kappa, iota and lambda, it fails to suggest or disclose a soft capsule formulation containing iota-carrageenan and a modified starch, such as hydroxypropylated tapioca starch.

U.S. Pat. No. 5,817,323 to Hutchison et al. discloses a composition for use in the shell of a comestible capsule comprising gelatin and a plasticizer, such as glycerol, together with a further compound which forms a secondary matrix for the plasticizer. This further component is disclosed as typically being unbleached potato starch acetate. This patent makes no suggestion or disclosure of the use of iota-carrageenan as an elasticizing agent for the film forming modified starches.

U.S. Pat. No. 4,804,542 to Fischer et al. describes gelatin capsules comprising a capsule sheath and a filling wherein the sheath contains a gelatin and at least 1% by weight of an agent selected from the group consisting of starches, starch derivatives, celluloses, cellulose derivatives, milk powder, non-hygroscopic mono-, di- and oligo saccharides, magnesium trisilicate and silicon dioxide. These agents are described as being capable of absorbing water in an amount of at least 10% by weight of its own weight. This patent teaches that the capsule sheath can then be used in containing water miscible, water soluble, water sensitive or hydrophilic materials. This patent makes no mention of iota-carrageenan.

U.S. Pat. No. 3,865,603 to Szymanski et al. relates to modified starch-extended gelatin compositions. This patent discloses modified starches with hydration temperatures above 99° C. for use with mammalian gelatin at weight ratios of about 1:9 to 1:1 (starch to gelatin). No mention is made of iota-carrageenan or the special need for soft capsule manufacture with sealing temperatures substantially below the melting point of the film.

SUMMARY OF THE INVENTION

The present invention provides compositions for manufacturing capsules, in particular, soft capsules, and especially soft capsules manufactured using the rotary die encapsulation apparatus. The invention provides compositions that do not employ mammalian gelatin and, therefore, overcome the disadvantages associated with collagen-derived material. Compositions of the invention do not contain any significant amounts of gelatin but, instead, require at least two (2) agents: 1) a modified starch having a hydration temperature below about 90° C. and 2) iota-carrageenan.

As those skilled in the art of soft capsule manufacture will appreciate, the film formed on the drum of the encapsulation machine is called the "wet film". This film is used in the rotary encapsulation machine to form the filled capsules. The capsules are then dried using any number of techniques. During the drying process, water is removed from the fill material (when the fill material is hydrophilic) and the capsule shell. The result is a soft capsule with a "dry film". The dry film comprises the various components, i.e., carrageenan, plasticizer, modified starch and the like and "bound water". The bound water, from about 6 to 12% by weight of the dry film, is not easily removable using conventional drying techniques and is not considered when describing the components of the dried film as a percentage of the composition. The dried film numbers are calculated numbers based upon a assumed weight percent of the bound water.

Thus, for example, Table I sets out the components of the inventive film forming composition and representative weight percent ranges for the wet film and the dry film.

TABLE I

| | Prototypic Formula | |
|---|---|---|
| Component | Weight % of Wet Film | Weight % of Dry Film |
| Iota-carrageenan | 6–12 | 12–24 |
| Modified starch | 12–30 | 30–60 |
| Plasticizer | 5–30 | 10–60 |
| Buffer | 0.5–2 | 1–4 |
| Preservative | 0–0.2 | 0–0.4 |

As will be demonstrated in the Examples, one aspect of the present invention resides in the discovery that the weight ratio of the modified starch to the iota-carrageenan is crucial to forming a satisfactory film. The weight ratio of the modified starch to the iota-carrageenan is at least 1.5:1, with a preferred range being 1.5:1 to 4:1. Another feature useful in characterizing the inventive film is fusion pressure. The mixture of modified starch, iota-carrageenan and other components should result in a wet film that fuses at pressures above 207 kPa.

Thus, there is disclosed, a composition suitable for forming a film for encapsulating materials, the composition comprising a modified starch and iota-carrageenan in a ratio by weight of at least 1.5:1; said film capable of fusion under a pressure of at least about 207 kPa (30 psi). There is further disclosed a composition wherein the weight ratio of modified starch to iota-carrageenan ranges from 1.5:1 to 4:1, more preferably from 2:1 to 3:1. Further, the invention relates to a film forming composition that is capable of fusion, under pressure, in the range of 207 kPa to 2070 kPa (30 to 300 psi) and at temperatures in the range of from 25–80° C. In a yet more preferred embodiment, the film according to the present invention has a melting temperature of from 2 to 25° C., more preferably 3–15° C. and most preferably 4–9° C. above its fusion temperature.

More specifically, the compositions according to the invention (expressed as wet film) comprise from 5–50% by weight modified starch; more preferably 15–40% by weight and the preferred modified starch is hydroxypropylated acid modified corn starch. The invention is also most preferably a composition wherein iota-carrageenan comprises at least 6 and up to 12% by weight of the composition. The composition according to the present invention may also contain a plasticizer such as glycerin and the plasticizer may comprise up to 50% by weight of the composition, more preferably up to 30% by weight.

There is also disclosed a dried film composition for soft capsules, the composition consisting essentially of from 42–84% by weight gel formers comprising a mixture of iota-carrageenan and modified starch; a plasticizer; and a buffer.

There is further disclosed a composition suitable for forming a soft capsule, the composition comprising iota-carrageenan and at least one modified starch selected from the group consisting of hydroxypropylated tapioca starch, hydroxypropylated maize starch, acid thinned hydroxypropylated corn starch, potato starch, pregelatinized modified corn starches, and wherein said starch has a hydration temperature below about 90° C. and wherein the weight ratio of modified starch in iota-carrageenan ranges from 1.5:1 to 4.0:1. The invention also relates to a soft capsule comprising a shell and a fill material wherein the shell is a film according to the present invention.

In general, the invention provides compositions that function effectively as replacements for the conventional mammalian gelatin based compositions. Thus, the compositions of the invention possess many of the desirable important characteristics of gelatin. The inventive compositions form films that are mechanically strong and exhibit elasticity sufficient to allow the film to stretch during filling (blow-molding). Thus, the invention films have dimensional stability, elasticity and strength adequate for use in a continuous process which requires their removal from a casting drum and subsequent transport to rotary dies. Unexpectedly, the fusion or sealing temperature is substantially less than the melting point of the inventive film. Thus, films formed from the compositions of the invention simultaneously fuse together during the filling and cutting portion of the rotary die process when subjected to sufficient pressure and elevated temperature.

An additional unexpected property of the films according to the invention is that sealing occurs at substantially lower pressures than those experienced with mammalian gelatin based compositions. For example, conventional mammalian gelatin based films seal at pressures of about 1,724 kPa (250 psi) whereas the new films according to the present invention seal at about 207 kPa, more preferably about 552 kPa (30–80 psi). This saves energy and reduces the wear experienced by the rotary die. Also, the inventive film, when dry, (the film contains about 6 to 12% by weight water) is durable and impermeable to hydrophobic liquids.

As used herein and in the claims, the term "fusion" is meant to mean the welding of two (2) films by the use of pressure so as to result in a bond that is not easily separated. The fusion of the two films during the rotary die process results in a seal that is adequate to hold the liquid fill of the soft capsule during its anticipated shelf life.

In a preferred embodiment, the invention provides compositions comprising at least one modified starch and iota-carrageenan in a ratio by weight in the range of 1.5:1 to 4:1; plasticizers; buffers and optionally preservatives. Such materials can be formed into films that have sufficient structure, elasticity and strength to be removed from a temperature-controlled casting surface. It has unexpectedly been found that a combination of carrageenan, especially iota-carrageenan, and at least one modified starch, forms films having characteristics that allow the film to be reversibly stretched during the capsule filling step. These compositions, as wet films, preferably comprise water, 6–12 weight % iota-carrageenan, 12–30 weight % modified starch, 5–30 weight % plasticizers, 0.5–2 weight % buffers and optionally 0–0.2 weight % preservatives.

In another embodiment, the invention provides films comprising water and a solids system. In the films of the present invention, the solid system comprises modified starch and iota-carrageenan. The films of the invention are capable of maintaining their form without being applied to a support; they do not lose their shape through splitting, lengthening, disintegration or otherwise by breakdown of the film when unsupported. However, the films may be stretched when pulled or compressed to a certain extent when an appropriate external force is applied.

As used herein and in the claims, the term "modified starch" includes such starches as hydroxypropylated starches, acid thinned starches and the like. The only native starch determined to be functional with iota-carrageenan in preparing the films according to the invention is potato starch, thereby the term "modified starch" is meant to include native, unmodified potato starch. In general, modified starches are products prepared by chemical treatment of starches, for example, acid treatment starches, enzyme treatment starches, oxidized starches, cross-bonding starches, and other starch derivatives. It is preferred that the modified starches be derivatized wherein side chains are modified with hydrophilic or hydrophobic groups to thereby form a more complicated structure with a strong interaction between side chains.

Through the diligent work of the inventors herein, they have determined that some starches are barely functional in their inventive compositions and include high amylose starches, native starches other than potato starch and cross-linked starches. Hydrogenated starch hydrolysates that have been used to promote the disintegration of the gelatin capsule would likewise not be useful in the present invention.

These are two characteristics that help characterize modified starches that are useful in the present invention and they are 1) hydration temperatures below about 90° C. and 2) film forming capabilities. Through a careful study of numerous starches, it has been determined that the following starches are not useful in the present invention: tapioca dextrin, high amylose non-modified corn starch, modified waxy maize starch, non-granular starch, modified high amylose corn starch and pregelatinized rice flour.

There is further disclosed an edible, soft capsule which comprises:

a) a soft, dry shell which comprises:
   (i) about 12–24 weight % iota-carrageenan;
   (ii) about 30–60 weight % modified starch;
   (iii) about 10–60 weight % plasticizer;
   (iv) about 1–4 weight % sodium phosphate dibasic buffer system; and
   wherein said shell encloses:
b) a soft capsule fill material.

In a further embodiment of the invention, there is disclosed a capsule wherein the plasticizer is comprised of glycerin or sorbitol or a mixture thereof and the modified starch is selected from modified corn starch, acid modified hydroxypropylated corn starch and hydroxypropylated acid modified tapioca starch.

Carrageenan has been known for decades as a useful food ingredient. While salt and sugar are rather simple food ingredients, technologically, carrageenans are rather complex and there are hundreds of different products available in the market called carrageenan with highly different price levels and functionalities. Carrageenan is obtained by aqueous extraction of natural strains of seaweeds of Gigartinaceae, Solieriaceae, Phyllophoraceae, and Hypneaceae, families of the class Rhodophyccae (red seaweeds). The three major forms of carrageenan are known as iota, kappa and lambda carrageenan. Lambda and kappa carrageenans do not typically occur together in the same plant, however, since the various species are harvested together, extraction yields a typical mixture of kappa and lambda with an average of around 70% kappa and 30% lambda. Euchema Spinosum is the seaweed source for production of iota-carrageenan either as an extract or as a processed Euchema seaweed. During the production of carrageenans, it is common that no sorting takes place before shipment of the seaweed to the carrageenan rendering facilities. Seaweeds are typically sold based on seaweed type and content of sand, salt, stones and humidity and not based on functional specifications. Thus, carrageenan manufacturers need to test each seaweed shipment to determine the quality of the extractable carrageenan in order to see if any processing adjustments are needed for obtaining the desired specifications. Carrageenans are available in the market place as standardized and non-standardized carrageenans. Standardization is done either by blending different pure carrageenan batches (cross-blending) or by blending one or more carrageenan batches with other ingredients such as salts (KCl, NaCl, and $CaCl_2$) and/or sugars (saccharose, dextrose, maltodextrins, lactose) in order to reach the desired specification. As used herein an in the claims, the recited weight percents for iota-carrageenan include the standardizing ingredient.

All carrageenans are water soluble gums having the common structural feature of being linear polysaccharides with a sugar backbone of alternating units consisting of galactose units linked by 1,3-β-D-linkages, as well as 1,4-α-D-linkages. The fundamental properties of iota, kappa and lambda are a function of the number and position of the ester sulfate groups. Iota-carrageenan contains approximately 30% by weight 3,6 anhydro-D-galactose and 32% ester sulfate by weight. In contrast, kappa carrageenan contains more than 36% by weight 3,6 anhydro-D-galactose and 32% ester sulfate by weight. Molecular weight ranges from 100,000 to 500,000 Daltons. The gelling carrageenans (kappa and iota) contain an "internal" ring—the 3,6-anhydro ring. The presence of ester sulfate makes carrageenans negatively charged at all pH values and is responsible for carrageenans being highly reactive molecules. Commercially available carrageenans are typically not well defined chemical compounds. However, through careful quality control, relatively pure materials with specified properties are available commercially.

The gelling carrageenan types (kappa and iota) are biosynthesized by the living seaweed as a non-gelling precursor, which is then turned into the gelling form by the action of the enzyme, dekinkase, which catalyzes the formation of the 3,6-anhydroglacatose ring. As mentioned previously, iota-carrageenan is only produced from Euchema Spinosum and produces the strongest gels with calcium ions ($Ca^{++}$). The gels are very elastic and completely syneresis free at the normal concentrations for food application (i.e., 0.5 to 2% by weight). Although iota-carrageenan does not gel with Na+, diluted iota-carrageenan solutions will form thixotropic solutions also with Na+ as it acts as a stabilizing agent. In the best mode of the present invention, the $Ca^{++}$ content is kept to a minimum.

In iota-carrageenan, the 1,3- and 1,4-linked units are respectively D-galactose-4-sulfate and 3,6-anhydro-D-galactose-2-sulfate. However, some of the 3,6-anhydro-D-galactose-2-sulfate rings may be replaced by D-galactose-6-sulfate, which may reduce considerably the gelling power of the iota-carrageenan.

The iota-carrageenan useful in the composition according to the invention should conform to the specification laid down by the USA and European regulatory authorities. The iota-carrageenan should not be degraded and should conform to minimum viscosity standards, which correspond to a molecular weight of about 100K Daltons.

Syneresis is often measured on carrageenan gels to determine breaking force and characterize the iota from the kappa carrageenan. After breaking force has been measured, the gel is transferred to a petri dish and covered to avoid evaporation from the gels. After typically about four (4) hours, the amount of free water (the syneresis) is measured. A high value indicates a strong gelling kappa, whereas no syneresis indicates iota.

Table II sets out typical analytical patterns and values for iota-carrageenan.

TABLE II

Typical Analytical Parameters and Values for Iota-carrageenan

| Parameter | Typical Values (Ca-iota) | Typical Values (Na-iota) |
|---|---|---|
| Gel strength | 0–100 g/cm$^2$ (1.5% carrageenan) | 0 |
| pH | 7–10 (i.e. 1.5% gel) | 7–10 |
| Viscosity | 10–30 cP (1.5% at 75° C.) | 10–30 |
| Chloride | 0–1% (as KCl) | 0–1% |
| Calcium | 2–6% | 0–0.5% |
| Sodium | ~1% | 3–5% |
| Potassium | 3–5% | 4–7% |

Through extensive investigative efforts, the inventors have determined that iota-carrageenan alone does not produce an acceptable film and that the modified starches alone do not produce a useable film for encapsulation. Without being bound to any theory or mechanism, it is speculated that the iota-carrageenan and modified starches interact synergistically to provide films of sufficient strength and elasticity to be useful in the encapsulation process.

The films made from the compositions of the invention possess the desirable properties of the films made from gelatin and function as effective replacements for gelatin films in virtually all processes that employ aqueous-gelatin compositions for the production of soft capsules. Among those processes are rotary die encapsulation processes, reciprocating die encapsulation processes, concentric cylinder processes, and processes for film-enrobing tablets. The film-enrobing process is also a rotary die process, as described in U.S. Pat. No. 5,146,730, the disclosure of which is incorporated herein by reference in its entirety. Thus, the compositions of the present invention provide:

i) mechanically strong, elastic films that set on a temperature-controlled casting drum generally within from about 15 to about 60 seconds, preferably less than about 20 seconds;

ii) films that, when brought into contact with one another, fuse together at temperatures of from about 25–80° C. and pressures of from about 207 to about 2070 kPa (30–300 psi);

iii) films that fuse (form seals in the rotary die process) at temperatures significantly below the melting point of the films; and iv) strong, durable dried films.

Still other advantages of the inventive compositions include:

i) finished capsules are not prone to cross-linking or insolubilization due to interaction with materials such as aldehydes, phenols ketones, that may be present within the capsule fill or shell, or that are formed over time by oxidization; and ii) finished capsules exhibit greater stability when exposed to elevated humidity and temperature than capsules made using gelatin.

The compositions of the present invention are capable of forming unsupported wet and/or dry films, i.e., the films do not require a support to maintain their shape and structure. Further, they do not disintegrate, tear or fracture unless some significant external force is applied. The compositions of the invention are formed into films by any of a variety of suitable methods. While casting or extruding onto a casting drum is preferred in connection with the rotary die process, other processes for forming films will be apparent to those skilled in the art.

Other components may also be incorporated into the compositions provided they do not alter the melting point/fusion point characteristics of the inventive film. Representative of these additional components include flavoring agents, opacifying agents, preservatives, embrittlement inhibiting agents, colorants and disintegrants. The inventive compositions are typically in the molten state when these components are added. Use of conventional pharmaceutical or food grade ingredients is acceptable.

As used herein and in the claims, the phrase "an amount of modified starch effective to form a structured film" means an amount of a modified starch sufficient to form a film or gel that does not flow, but has dimensional stability. More preferably, the phrase "effective to form a structured film" means an amount of a modified starch sufficient to form a dimensionally stable film having a thickness of at least about 0.01 inches.

The phrase "effective elasticizing amount" means an amount of iota-carrageenan sufficient to provide a starch based composition in the form of film with sufficient strength to be removed from a casting drug during rotary die processing and also sufficient elasticity to be deformed during the rotary die process when a fill material is presented between a pair of films of the composition (blow molded).

The phrase "fusion temperature" means the temperature at which two opposing films, in contact with each other, will blend at their contact interface to become one, indistinguishable and inseparable structure.

The weight ratio of modified starch to iota-carrageenan in this invention is at least 1.5:1, more preferably from about 1.5:1 to about 4:1, most preferably, from about 2:1 to about 3:1. Unexpectedly, the compositions of the invention possess the important characteristic of having a melting point temperature that is substantially higher than the fusion temperature. Preferably, the melting point temperature of a film according to the invention, is from about 3–15° C., and more preferably from about 4 to 9° C., above its fusion temperature.

While not being bound to any theory or mechanism, it is believed that the iota-carrageenan functions as an elasticizing agent. In other words, this elasticizing agent renders an otherwise in-elastic, modified starch film, elastic. Consequently, the films of the invention have a "memory" and are capable of returning substantially to their original size and shape after being subjected to a deforming force. For example, a film made from the starch/carrageenan compositions of the invention that is stretched along its length and/or width will substantially return to its original length over time.

As discussed previously, the modified starches useful in the present invention include those starches that have a hydration temperature below about 90° C. Hydration temperatures for most starches are available in the literature, such as product data for commercially available starches. Where they are not available via the literature, such hydration temperatures may be readily determined employing techniques well know to those skilled in the art. Suitable starches also must be capable of forming an aqueous mixture with water at a concentration of at least from about 20 weight % to give a mixture having a viscosity below about 60,000 to 80,000 centipoise (cps) measured at a 10 sec-1 shear rate at the temperature at which starch hydration occurs.

Representative of the commercially available starches useful in the present invention include Pure Cote™ B760 and B790 (an acid-modified hydroxypropylated corn starch), Pure-Cote™ B793 (a pre-gelatinized modified corn starch), Pure-Cote™ B795 (a pre-gelatinized modified corn starch), and Pure-Set™ B965 (a flash-dried acid modified native corn dent starch), all available from the Grain Processing Corporation of Muscatine, Iowa. Other useful, commercially available, modified starches include C*AraTex™ 75701 (hydroxypropylated acid modified tapioca starch), available from Cerestar, Inc. of Hammond, Ind.; M250 and M180 (maltrins) and Pure-Dent™ B890 (modified corn starch) from Grain Processing Corporation; and Midsol Crisp (modified high amylose corn starch) from Midwest Grain, Inc. of Atkinson, Kans. The only native (unmodified) starch suitable for use herein is potato starch. Such a starch is available from Roquette as Potato Starch Supra Bacter.

The invention may include genetically (recombinantly) modified and hybridized starches. Genetically modified and hybridized starches include those that have been developed to alter the physical properties and/or the amylose/amylopectin ratios. The preferred starch is an acid hydrolyzed corn starch modified with 2-hydroxypropyl ether functional groups. This starch is identified by Chemical Abstracts Service Registry No. 68584-86-1. This material is commercially available as PURE-COTE® B760 and B790 from Grain Processing Corporation.

The iota-carrageenan is present in the inventive compositions in an amount that, in combination with starch, effectively causes the compositions to have the required gelatin-like functional properties. As discussed previously, as those skilled in the art will appreciate, the film has what is known as a wet shell composition and a dry shell composition. This results from the evaporation of water from the film during the manufacturing process of the soft capsule. Preferred amounts of iota-carrageenan range from about 6 to 12% by weight of the wet shell composition. More preferred amounts of iota-carrageenan range from about 7–12% by weight of the wet composition. Particularly preferred compositions contain from about 9–11 weight % of iota-carrageenan, based on the weight of the wet composition. Even more preferred compositions contain about 10 weight % of iota-carrageenan by weight of the wet composition.

As will be demonstrated in the Examples, not all members of the carrageenans family can be used herein. Standardized iota-carrageenans are preferred. A particular preferred standardized iota-carrageenan is commercial available from the FMC Corporation of Princeton, N.J., known as VISCARIN® SD389, standardized with 15% by weight dextrose. Other useful iota-carrageenans include a non-standardized iota-carrageenan from SKW BioSystems of Baupt, France known as XPU-HGI and a non-standardized iota-carrageenan from FMC.

In general, the film forming compositions may consist of the iota-carrageenan, at least one modified starch with the balance of the composition being water. However, preferred compositions of the invention include a plasticizer. Suitable plasticizers include the materials used for the same purpose in the manufacture of mammalian gelatin capsules. Representative plasticizers are any of a variety of polyhydric alcohols such as glycerin, sorbitol, propylene glycol, polyethylene glycol and the like. Other plasticizers include saccharides and polysaccharides. The saccharides and polysaccharides suitable for use herein may be produced by hydrolysis and/or hydrogenation of a simple or complex polysaccharides.

Where plasticizers are employed, they can be used in amounts of up to about 60% by weight of the dry shell composition or 30% of the wet shell composition. More preferred compositions contain from about 10 to 25% by weight, based on the weight of the wet shell composition and 30–50% by weight of the dry shell composition.

Also, the capsule forming composition, i.e., the shell mass composition, may optionally contain an embrittlement inhibiting composition. An example of embrittlement inhibiting compositions is a mixture of sorbitol and one or more sorbitans. See U.S. Pat. No. 4,780,316.

Optionally, the film forming composition may contain preservatives and stabilizers such as mixed parabens, ordinarily methyl or propyl parabens, in about a 4:1 ratio. The parabens may be incorporated in the compositions at levels of 0–0.2 weight % for the wet shell and 0–0.4 weight % for the dry shell. It should be noted that in the following Examples, preservatives were included in the experimental formulation to facilitate un-dried sample retention for later evaluations. Without preservatives, the retained wet ribbons would be spoiled by microbial growth in a day or two. On a commercial scale, preservatives would typically note be added to the film forming composition because the wet ribbon would be quickly processed through the encapsulation machines and then the dryers. The dried film does not support microbial growth.

It has been found by the inventors that the use of a buffer system in the inventive compositions is highly desirable. Any known buffer can be used with phosphate buffers being preferred. Controlling the pH of the melt and film is highly important as carrageenans are rapidly broken down in conditions of high temperature and acidity. As mentioned previously, the presence of $Ca^{++}$ ions should be kept to a minimum.

Soft capsules may be manufactured in accordance with conventional techniques as set forth in Ebert, E. W., "Soft elastic gelatin capsules: a unique dosage form", Pharmaceutical Tech., October 1977; Stanley, J. P., "Soft Gelatin Capsules", in The Theory and Practice of Industrial Pharmacy, 359–84 (Lea and Febiger ed. 1970); U.S. Pat. Nos. 1,970,396; 2,288,327; and 2,318,718.

The capsules made using the rotary die process, will typically have wet shell thicknesses varying from about 0.024 to 0.1778, preferably from about 0.0508 to 0.127 and more preferably from about 0.0508 to 0.0762 cm in thickness. The capsules of the invention may be manufactured in any desired shape using the above-mentioned rotary die process.

The fill materials for the soft capsules may be any of a wide variety of materials suitable for encapsulation using the rotary die apparatus. Among the types of materials that are suitable for encapsulation include oils, hydrophilic liquids and emulsions. The active components that may be contained within the oils and emulsions are hydrophobic and hydrophilic actives. Those skilled in the art are familiar with and will recognize suitable fill materials. These fill materials may contain cosmetics, foods including vitamins, liquids, semi-solids, suspensions, flavorings and pharmaceuticals. After filling, the capsules are typically dried according to conventional techniques, e.g., tray drying, using a drum dryer or other suitable drying methods.

DETAILED DESCRIPTION OF THE PREFERRED EMBODIMENTS

The following examples demonstrate certain aspects of the present invention. However, it is to be understood that these examples are for illustrative purposes only and do not purport to be wholly definitive as to conditions and the scope of this invention. It also should be appreciated that when typical reaction conditions (e.g., temperature, reaction times) have been given, the conditions which are both above and below these specified ranges can also be used, though generally less conveniently.

A further understanding of the invention may be obtained from the following non-limiting examples. Each of the following compositions is prepared according to the method described below. All temperatures are expressed in degrees Celsius (° C.) and all parts are parts by weight, unless designated otherwise.

EXAMPLE 1

Preparation of the Capsule Shell Material

A mixer, fitted with suitable medium shear mixing blades, and a side sweep assembly was used to prepare a molten mass for forming films. The mixing container may be heated or cooled as needed and optionally may be constructed such that a vacuum can be established inside the vessel.

Appropriate quantities of each component (except starch and carrageenan) for each formulation was added to the mixer and blended. The starch and carrageenan were then added to the mixture and mixed under vacuum. Heat and continuous stirring were applied until the mixture became molten and homogeneous. Samples from each formulation were taken and cast onto a glass plate that was at room temperature. A blade or draw bar with a notch of about 15 cm in width and 0.127 cm in height was used to create the casting. After cooling, the film (about 0.06 cm to 0.08 cm in thickness) was evaluated for stiffness, elasticity, brittleness and film strength. Those films that were characterized by the investigator as having some potential were evaluated for sealing properties. The film was carefully removed from the glass plate and folded in half and placed on a preheated bag sealer from Midwest Pacific Corp. The arm was lowered and contacted the folded film as heat and pressure were applied. This device is also known as an impulse sealer and was used to assess the sealability of wet films in the laboratory. This device provided a good guide as to whether or not an experimental film would form a seal. The fusion of the two films was then observed and rated as a weak seal or a good seal. The molten mass was subsequently charged into a heated, preferably electrically heated holding tank and maintained in its molten state until needed for encapsulation, if the formulation was to be used for encapsulation. Normal rotary die pressures for gelatin films range from 200–300 lbs. (19–136 kg). It was determined from this work that sealing pressure reductions of greater than 50% (34–68 kg) could be realized and still produce a good seal.

The following formulations were prepared as discussed above.

Formulation 1

| Ingredient | Wet Film Percent by Weight | Dry Film* Percent by Weight |
|---|---|---|
| PURE-COTE ® B790 | 15.0 | 33.94 |
| VISCARIN ® SD389** | 8.0 | 15.38 |
| Glycerin USP (plasticizer) | 20.0 | 45.25 |
| Sodium phosphate di basic (buffer) | 1.0 | 2.26 |
| Preservative (parabens) | 0.20 | 0.45 |
| Water USP | 55.8 | |
| Dextrose | | 2.71 |

Formulation 2

| Ingredient | Wet Film Percent by weight | Dry Film* Percent by weight |
|---|---|---|
| PURE-COTE ® B790 | 15.0 | 34.32 |
| VISCARIN ® SD389** | 10.0 | 19.45 |
| Glycerin USP (Plasticizer) | 17.5 | 40.05 |
| Sodium phosphate di basic (buffer) | 1.0 | 2.29 |
| Preservative (parabens) | 0.20 | 0.48 |
| Water USP | 56.3 | |
| Dextrose | | 3.43 |

Formulation 3

| Ingredient | Wet Film Percent by weight | Dry Film* Percent by weight |
|---|---|---|
| PURE-COTE ® B760 | 22.0 | 37.29 |
| VISCARIN ® SD389** | 10.0 | 14.41 |
| Glycerin USP | 25.8 | 43.73 |
| Sodium phosphate di basic | 1.0 | 1.69 |
| Preservative | 0.20 | 0.34 |
| Water USP | 41.0 | |
| Dextrose | | 2.54 |

Formulation 4

| Ingredient | Wet Film Percent by weight | Dry Film* Percent by weight |
|---|---|---|
| PURE-COTE ® B760 | 28.0 | 49.56 |
| VISCARIN ® SD389** | 11.0 | 16.55 |
| Glycerin USP | 15.8 | 27.96 |
| Sodium phosphate di basic | 1.5 | 2.65 |
| Preservative | 0.20 | 0.35 |
| Water USP | 43.5 | |
| Dextrose | | 2.92 |

Formulation 5

| Ingredient | Wet Film Percent by weight |
|---|---|
| PURE-COTE B790 ® | 27 |
| Genuvisco TPM-1 ® | 10 |
| Glycerin USP | 20 |
| Water USP | 43 |

Formulation 6

| Ingredient | Wet Film Percent by weight |
|---|---|
| LYCATAB pregelatinized starch (Roquette) | 27.3 |
| VISCARIN ® SD389 | 10.0 |
| Glycerin USP | 15.0 |
| Sodium phosphate di basic | 1.0 |
| Preservative | 0.20 |
| Water USP | 46.5 |

Formulation 7
Native Potato Starch

| Ingredient | Wet Film Percent by weight |
|---|---|
| Potato Starch Supra Bacter (Roquette) | 15.8 |
| Iota-carrageenan | 8.0 |
| Glycerin USP | 15.0 |
| Sodium phosphate di basic | 1.0 |
| Preservative | 0.20 |
| Water USP | 60.0 |

Formulation 8

| Ingredient | Wet Film Percent by weight | Dry Film Percent by weight |
|---|---|---|
| PURE-COTE ® B790 | 23.5 | 41.96 |
| Iota-carrageenan XPU-HGI (SKW) - (not available) | 8.5 | 15.18 |
| Glycerin USP | 23.0 | 41.07 |
| Sodium phosphate di basic | 3.0 | 1.79 |
| Water | 44.0 | |

Formulation 9
Kappa only - no iota

| Ingredient | Percent by weight |
|---|---|
| PURE-COTE ® | 20.0 |
| Kappa-carrageenan | 6.0 |
| Xanthan gum | 2.0 |
| Glycerin USP | 20.0 |
| Sodium phosphate di basic | 1.0 |
| Preservative | 0.20 |
| Water USP | 50.8 |

Formulation 10

| Ingredient | Wet Film Percent by weight | Dry Film Percent by weight |
|---|---|---|
| PURE-COTE ® B760 | 23.0 | 40.03 |
| VISCARIN ® SD389** | 10.45 | 15.46 |
| Glycerin USP | 23.0 | 40.03 |
| Sodium phosphate di basic | 1.0 | 1.74 |
| Water USP | 42.55 | |
| Dextrose | | 2.73 |

*Drive Film Values Calculated
**Standardized with 15% by weight dextrose
Note: In the dry film calculations, the dextrose content, from the iota carrageenan is set out separately.

Formulations 1, 3, 4, 6, 8 and 10 all produced excellent films that displayed excellent elasticity and sealing features. Formulation 2 produced a seal, but of a weak character compared to Formulations 1, 3 and 4. This could be the result of the modified starch to iota-carrageenan ratio of 1.5:1, whereas Formulations 3 and 4 had starch to carrageenan weight ratios in excess of 2.0:1. Formulation 5 yielded a good film, but the sealing characteristics were poorer than Formulations 3 and 4; this could be due to the high, 2.7:1, starch to carrageenan ratio. Formulation 7, the only unmodified starch that was found to work with iota-carrageenan was found to cast an acceptable film that evidenced good sealing properties. In contrast, Formulation 9, kappa carrageenan only—no iota, produced a brittle film that could not be sealed. This experiment evidences that kappa carrageenan is not a substitute for iota in the present invention.

EXAMPLE 2

Rotary Die Process

A standard rotary die machine (see The Theory and Practice of Industrial Pharmacy, Lachmnan, Lieberman and Kanig, Editors, 3rd Edition, published by Lea & Febiger, was used to attempt the manufacture of filled capsules using Formulations 1–4, 6, 8 and 10. The fill material was provided to the hopper connected to the rotary die encapsulation machine. The hopper was heated and jacketed. Ribbons of casting material were formed in any of a variety of conventional methods, including extrusion or gravity feed of the liquid Formulations 1–4, 6, 8 and 10 onto a revolving casting drum. The formulations were provided to the drum generally at a temperature 2–5° C. above the melting point of the formulation. This temperature varies according to each specific formulation. Encapsulation of the fill material between two ribbons of the film was carried out according to conventional procedures.

Capsules prepared according to conventional rotary die procedures using Formulations 1, 3, 4 and 10, as set forth in this example, produced durable capsules that, upon drying, are similar in appearance to traditional softgels manufactured from mammalian gelatin.

EXAMPLE 3

Evaluation of Capsule Properties

Capsules produced according to Examples 1 and 2 above were tested for disintegration and resistance to accelerated storage conditions. Samples of dried capsules were tested using a standard USP disintegration apparatus fitted with guided disks. The test medium was 0.1 M HCl maintained at 37° C. Capsules ruptured within 3 minutes and the shell disintegrated within 15 minutes. These results are comparable to those obtained using a conventional soft mammalian gelatin capsule.

Additional samples were stored in open containers for 3 months at 40° C./75% Relative Humidity ("RH"), which is a standard condition used to accelerate stability evaluation of pharmaceutical dosage forms. A mammalian gelatin based softgel filled with mineral oil was also evaluated using the same conditions as a control. The modified starch/iota-carrageenan capsules remained structurally intact and exhibited only softening of the shell. In contrast, the mammalian based soft capsules had fused together and lost much of their structural integrity. Thus, the capsules made according to the invention exhibited superior resistance to humidity and temperature compared to conventional mammalian gelatin-based soft capsules.

EXAMPLE 4

Comparative Analysis

The following is a comparison of capsule shell formulation characteristics and associated rotary die parameters for conventional mammalian gelatin-based materials, a composition wherein the film was formed solely from carrageenan, and a modified starch/iota-carrageenan compositions according to the present invention. The only carrageenan composition was made essentially according to the description set forth in published International Application WO 97/07347, except that 17% carrageenan is used instead of 9% as described in the International Application. Table III sets forth the melting point of each composition in addition to processing conditions specific to each composition for use in the rotary die process.

TABLE III

| | CONTROL Gelatin | INVENTION Starch/Carrageenan | CONTROL Carrageenans |
|---|---|---|---|
| Formulation | 30–45% gelatin; 10–30% plasticizer, water q.s. | 15–20% starch; 8–10% iota-carrageenan | 17% iota-carrageenan |
| Typical Melt Temperature | 50–55° C. | 80–85° C. | 95–98% |
| Operational Casting | 60–65° C. | About 90–95° C. | 98–100° C. |
| Fusion Temperature for sealing (Wedge Temperature) | 40–42° C. | 53–75° C. | 98–100° C. |
| Pressure | 100–300 psi | 50–200 psi | Not determined* |
| Typical Ribbon thickness (inches) | 0.28–0.040 | 0.020–0.025 | Not determined* |
| Machine speed (optimum) | 2 to 3 rpm | 2 to 6 rpm | Not determined* |

*The sealing (wedge) temperature was adjusted to the temperature at which the material fuses, 98–100° C., which is also the melting temperature. No fusion takes place at lower temperatures. Sealing and production of capsules was attempted, but the ribbon melted at the wedge. No capsules were formed.

This Example supports the conclusion that the starch/carrageenan compositions of the present invention possess properties similar to mammalian gelatin and therefore allow for their satisfactory use in the rotary die process. In contrast, the film forming composition taught in WO 97/07347 is not acceptable for forming soft capsules.

Films derived from compositions containing carrageenan as the only film forming material do not possess the desired properties of gelatin films and are therefore unsuitable for use in the rotary die process.

EXAMPLE 5

The following Formulations were prepared as set forth in Example 1, except that they were prepared on a 500 gm scale. The prepared formulations, as set forth in Table IV, were cast onto a glass plate using a draw bar set between 0.10 and 0.127 cm in height (0.040 to 0.050 inches) to form ribbons as described in Example 1. The ribbons of film were evaluated wet and then allowed to set/dry overnight and then revaluated. Ribbon strength, elasticity, clarity, texture and thermal sealing were measured. All values are weight % unless noted otherwise.

TABLE IV

| Component | #11 | #12 | #13 | #14 | #15 | #16 | #17 | #18 | #19 | #20 | #21 | #22 | #23 | #24 | #25 | #26 | #27 |
|---|---|---|---|---|---|---|---|---|---|---|---|---|---|---|---|---|---|
| | Weight Percent Wet Film | | | | | | | | | | | | | | | | |
| [1]Kappa carrageenan | 5.65 | 5.65 | 10.0 | 10.0 | 5.0 | 2.5 | 1.0 | 10.0 | 8.0 | 10.0 | 10.0 | 10.0 | | | | | |
| [1]Lambda carrageenan | 5.65 | | | | | | | | | | | | | | | | |
| [1]Iota carrageenan | | 5.65 | | | 5.0 | 7.5 | 9.0 | | | | | | | | | | |
| [2]Pure Cote ™ B760 | | | 15.0 | 22.0 | 27.3 | 27.3 | 27.3 | 13.55 | 20.0 | 20.0 | 20.0 | 23.0 | | 27.3 | | 20.0 | 15.0 |
| Water | 80.2 | 80.2 | 56.3 | 41.0 | 46.5 | 46.5 | 46.5 | 45.0 | 45.0 | 48.3 | 48.3 | 42.8 | 68.8 | 46.5 | 74.5 | 50.0 | 55.0 |
| Glycerin | 8.3 | 8.3 | 17.5 | 25.8 | 15.0 | 15.0 | 15.0 | 30.0 | 25.8 | 20.0 | 20.0 | 22.0 | 20.0 | 15.0 | 20.0 | 20.0 | 20.0 |
| Preservative | 0.2 | 0.2 | 0.2 | 0.2 | 0.2 | 0.2 | 0.2 | 0.2 | 0.2 | 0.2 | 0.2 | 0.2 | 0.2 | 0.2 | | | |
| $Na_2HPO_4$ | | | 1.0 | 1.0 | 1.0 | 1.0 | 1.0 | 1.0 | 1.0 | 1.0 | 1.0 | 1.0 | 1.0 | 1.0 | | | |
| Locust Bean Gum | | | | | | | | 0.25 | | | 0.5 | 1.0 | | | | | |
| Xanthan Gum | | | | | | | | | | 0.5 | | | | | | | |
| [3]XPU-APK Kappa carrageenan | | | | | | | | | | | | | 10.0 | 10.0 | | | |
| [3]XPU-CMI Iota/Kappa blend | | | | | | | | | | | | | | | 5.5 | 10.0 | 10.0 |

[1]Supplied by FMC Corporation of Princeton, New Jersey
[2]Hydroxypropylated maize starch
[3]Supplied by SKW Biosystems The formulations containing kappa carrageenan, F11 to F23, all produced a brittle and weak film irrespective of the level of the modified starch (Pure Cote B790). Even the inclusion of lambda carrageenan (F11) or iota-carrageenan (F12, F15–F17) to the kappa did not produce a useable film. Even F17 with 1% kappa, 9% iota and 27.3% modified corn starch (Pure Cote B790) produced a non-brittle film that only formed a weak seal. Thus, the presence of even low levels of kappa carrageenan is detrimental to the production of a useable film.

EXAMPLE 6

Using the procedure set forth in Example 5, additional formulations were prepared and evaluated. The formulations are set forth in Table V.

TABLE V

| Component | #28 | #29 | #30 | #31 |
|---|---|---|---|---|
| [1]Lambda carrageenan | 10.0 | | | |
| [1]Iota-carrageenen LC-5 standardized with sacrose | | 10.0 | | |
| Pure Cote ™ B790 | 15.0 | 27.3 | 27.3 | |
| [2]TPH-1 non-standardized iota | | | 10.0 | |
| [3]XPU-HG1 iota | | | | 10.0 |
| Water | 56.3 | 46.5 | 46.5 | 68.8 |
| Glycerin | 17.5 | 15.0 | 20.0 | 20.0 |
| $Na_2HPO_4$ | 1.0 | 1.0 | 1.0 | 1.0 |
| Preservative | 0.2 | 0.2 | 0.2 | 0.2 |

[1]Supplied by FMC Corp.
[2]Supplied by Hercules Corp.
[3]Supplied by SKW Biosystems F28 (lambda carrageenan plus modified starch) produced a very weak film that did not seal. In contrast F29 and F30 (iota-carrageenan plus modified starch) produced very strong films that provided excellent seals. F31 (iota only) produced a strong film, but would not seal.

EXAMPLE 7

Using the procedure set forth in Examples 1 and 2, the following formulations were prepared cast onto a rotary encapsulation machine and formed into soft capsules filled with vitamin E.

TABLE VI

| Component | #32 Wet film | #32 Dry film | #33 Wet film | #33 Dry film |
|---|---|---|---|---|
| Viscarin SD-389 Standardized iota | 10.25 | 14.97 | 0 | 0 |
| Pure Cote B760 | 25.75 | 44.25 | 24.0 | 41.96 |
| Glycerin | 21.0 | 36.08 | 22.5 | 39.34 |
| Sodium phosphate buffer | 1.0 | 1.72 | 1.0 | 1.75 |
| Parabens | 0.2 | 0.34 | 0.2 | 0.35 |
| Water | 41.8 | | 42.8 | |
| XPU HG1 | | 2.64 | 9.5 | 15.61 |

F32 and F33 were found to be easily processed on the rotary die encapsulation machine. These formulations represent the inventors best mode and produced capsules with very few defects. The capsules were then tested in a simulated gastric fluid and were found to dissolve or disintegrate in about five (5) minutes, which is about the time for commercially available mammalian gelatin capsules.

EXAMPLE 8

In this experiment, hydroxypropylated tapioca starch was used in combination with iota-carrageenan to produce a soft capsule. The tapioca formulation #34, and a comparative maize formulation are set forth in Table VII.

TABLE VII

| Component | #34 | #35 |
|---|---|---|
| | Weight % In Wet Composition | |
| Iota-carrageenan (Viscarin SD389) | 10.25 | 10.25 |
| Hydroxypropylated tapioca starch | 25.75 | 0 |

TABLE VII-continued

| Component | Weight % In Wet Composition #34 | #35 |
|---|---|---|
| Glycerin | 21.40 | 21.40 |
| Disodium phosphate | 41.60 | 41.60 |
| Water | 1.0 | 1.0 |
| Hydroxypropylated maize starch | 0 | 25.75 |

Soft capsules were manufactured successfully using a pilot scale encapsulation machine using F34 and F35. Yield is a measure of process effectiveness. It is expressed as the percentage of capsules that did not leak after drying, out of the number of capsules produced. The yield, using the hydroxypropylated maize starch, was slightly better than the modified tapioca starch. Formulation #35 has been used to produce over 100,000 soft capsules filled with vitamin E. The yield for this production run was found to be 99.1%, which is considered excellent.

EXAMPLE 9

Comparative

The formulation set forth in Table VIII investigates the use of kappa carrageenan as the sole elasticizing agent, as it is less expensive than iota-carrageenan.

TABLE VIII

| Component | Weight % in Wet Composition #34 |
|---|---|
| Kappa carrageenan | 8.0 |
| Locust Bean Gum | 0.5 |
| Xanthan Gum | 0.25 |
| Hydroxypropylated maize starch Pure Cote B790 | 18.00 |
| Glycerin | 30.2 |
| Disodium phosphate | 1.0 |
| Water | 42.05 |

Formulation #34 was placed on a pilot scale rotary die encapsulation machine and was not successful in producing any intact soft capsules. The formulation would form films, but due to poor mechanical strength, low elasticity coefficient and inability to form seals, no soft capsules could be produced.

Industrial Applicability

The economic manufacture of soft capsules requires that the ribbons used to form the gels possess certain specific properties. While mammalian gelatin has remained the gelling agent of choice, there are numerous shortcomings that the pharmaceutical industry would like to overcome with new, non-gelatin soft capsules.

The present invention, which is founded in a discovery regarding the synergistic activity between a specific form of carrageenan and certain modified starches, will provide to the pharmaceutical industry an alternative to mammalian gelatin. It was through diligent experimentation and scientific observation that the inventive compositions were realized.

In the foregoing, there has been provided a detailed description of preferred embodiments of the present invention for the purpose of illustration and not limitation. It is to be understood that all other modifications, ramifications and equivalents obvious to those having skill in the art based on this disclosure are intended to be within the scope of the invention as claimed.

We claim:

1. An edible, soft capsule which comprises a soft, dry shell which comprises:

[(v)] (*a*) about 12–24 weight % iota-carrageenan;

[(vi)] (*b*) about 30–60 weight % modified starch;

[(vii)] (*c*) about 10–60 weight % plasticizer; *and*

[(viii)] (*d*) about 1–4 weight % sodium phosphate dibasic buffer system[; and], wherein said shell encloses a soft capsule fill material.

2. A soft capsule according to claim 1 wherein the plasticizer is comprised of glycerin or sorbitol or a mixture thereof and the modified starch is selected from the group consisting of modified corn starch, acid modified hydroxypropylated corn starch and hydroxypropylated acid modified tapioca starch.

*3. An edible, soft capsule which comprises a soft, dry shell which comprises:*

(*a*) *iota-carrageenan;*

(*b*) *modified starch; and*

(*c*) *plasticizer,*

*wherein the weight ratio of iota-carrageenan to modified starch is at least 1.5:1 and wherein said shell encloses a soft capsule fill material.*

*4. An edible, soft capsule which comprises:*

(*a*) *a soft dry shell comprising:*

(*i*) *iota-carrageenan;*

(*ii*) *modified starch; and*

(*iii*) *plasticizer,*

*wherein the weight ratio of iota-carrageenan to modified starch is at least 1.5:1, and*

(*b*) *soft capsule fill material.*

*5. A soft shell capsule according to claim 4 wherein the soft, dry shell also comprises buffer.*

*6. An edible, soft capsule, which comprises a soft, dry shell which comprises:*

(*a*) *about 12–24 weight % iota-carrageenan;*

(*b*) *about 30–60 weight % modified starch;*

(*c*) *about 10–60 weight % plasticizer; and*

(*d*) *about 1–4 weight % buffer,*

*wherein said shell encloses a soft capsule fill material.*

* * * * *